United States Patent [19]

DeFrank et al.

[11] 4,259,187

[45] Mar. 31, 1981

[54] INTRAVENOUS FLUID FILTER

[75] Inventors: Michael P. DeFrank, Woodstock; Joseph A. Bancsi, Vernon Hills, both of Ill.

[73] Assignee: Baxter Travenol Laboratories, Inc., Deerfield, Ill.

[21] Appl. No.: 46,426

[22] Filed: Jun. 7, 1979

[51] Int. Cl.[3] .............................................. B01D 35/02

[52] U.S. Cl. .................................... 210/446; 210/451; 210/496; 210/510; 210/927; 128/214 R

[58] Field of Search ............... 210/419, 435, 446, 451, 210/496, 510, DIG. 23; 128/214 R, 214 C

[56] References Cited

U.S. PATENT DOCUMENTS

| | | | |
|---|---|---|---|
| 2,297,817 | 10/1942 | Truxell et al. | 210/510 X |
| 2,378,949 | 6/1945 | Post | 210/510 X |
| 2,604,958 | 7/1952 | Leufvenlog | 55/523 X |
| 2,816,545 | 12/1957 | Jacoby | 128/214 |
| 2,982,418 | 5/1961 | Balley | 210/448 |
| 3,008,570 | 11/1961 | Roehr et al. | 210/DIG. 24 |
| 3,048,537 | 8/1962 | Pall et al. | 210/510 |
| 3,121,685 | 2/1964 | Hazell | 210/446 |
| 3,193,993 | 7/1965 | Barton et al. | 55/385 |
| 3,306,291 | 2/1967 | Burke | 128/218 |
| 3,322,114 | 5/1967 | Portnoy et al. | 128/2 |
| 3,515,282 | 6/1970 | Westesson | 210/496 X |
| 3,662,752 | 5/1972 | Yokoyama | 128/214 R |
| 3,744,640 | 7/1973 | Grover | 210/463 |
| 3,753,500 | 8/1973 | Voegeli | 210/446 |
| 3,817,389 | 6/1974 | Weichselbaum | 210/448 |
| 3,865,731 | 2/1975 | Seitz | 210/359 |
| 3,868,973 | 3/1975 | Bierman et al. | 210/DIG. 23 |
| 3,882,026 | 5/1975 | McPhee | 210/446 |
| 3,933,652 | 1/1976 | Weichselbaum | 210/446 |
| 3,969,250 | 7/1976 | Farr | 210/359 |
| 3,976,529 | 8/1976 | Weichselbaum | 210/510 X |

*Primary Examiner*—John Adee
*Attorney, Agent, or Firm*—Paul C. Flattery; John P. Kirby, Jr.; Gary W. McFarron

[57] ABSTRACT

A fluid filter is disclosed for use in filtering intravenous fluids as they are administered to a patient. The unique filter employs a normally hydrophobic (water-repellent) depth-type filter element, which has a sufficiently large pore size and volume of pores to permit an adequate gravitational flow of intravenous fluid from an elevated reservoir. Particulate matter is filtered out by the tortuous passageways in the filter element, through which liquid must pass. Due to the relatively large pore size (20 microns or larger) of the filter element, in combination with the normal hydrophobic property, any gas entrained in the liquid also passes through the filter element and does not accumulate on the filter surface to block flow therethrough—so called "air blocking".

24 Claims, 3 Drawing Figures

INTRAVENOUS FLUID FILTER

The present invention generally relates to fluid filter and, more particularly, to filters employed to remove particulate from intravenous fluids as they are administered to a patient.

In the administration of parenteral fluids or the like to a patient, it is often desirable to provide an in-line microporous filtration to insure that particulate matter is not passed to the patient. Typical in-line filter devices have used thin, relatively fragile microporous membranes for filtering out particulate. One aspect of employing a microporous filtering membrane, however, is that once the membrane is wetted by the filtering liquid, it becomes relatively impermeable to gas. This is sometimes referred to as the "hydrophilic" property of the material. If there is enough gas entrained in the fluid stream, it may accumulate on the surface of the filtering membrane until it completely covers it, blocking any further liquid flow through the filter membrane—often called "air-blocking". A further drawback with membrane type filters is that the "particle holding" capacity is limited to the surface area of the filter. That is, when filtering fluids with high levels of particulate, the filter may exhibit a reduced flow rate because of particle accumulation on the surface which partially blocks passage through the microscopic pores. In addition, membrane type filters often require reinforcement for use in a high-pressure IV pump applications, where forces arising from the pumping action could damage an unreinforced filter membrane.

Air-blocking has been avoided in at least one commercially successful filter device sold by Travenol Laboratories, Inc., of Deerfield, Illinois under the trademark MP5. As described in U.S. Pat. No. 4,004,587, that filter employes hydrophilic and hydrophobic (liquid-repellent) filters in a parallel flow relationship. Liquid passes through the hydrophilic filter membrane, and gas passes through the hydrophobic membrane before it can accumulate to block liquid flow. Although this filter device performs well, the filter membranes are thin and fragile and sometimes difficult to handle in the manufacturing process.

Stainless steel frit filters have also been used for filtering IV fluids and the like. For example, a stainless steel frit-type filter is shown in U.S. Pat. No. 3,933,652. However, these filters are complex and expensive to make and may require special installation techniques and equipment. Compare, e.g., U.S. Pat. No. 3,817,389.

Accordingly, it is a general object of the present invention to provide an improved intravenous fluid filter that does not suffer from the deficiencies described above.

It is a more specific object of the present invention to provide a microporous filter for intravenous fluid that does not "air-block".

It is another object of the present invention to provide a filter that has improved particle retention properties, and may be used in high pressure IV pump applications.

It is a further object of the present invention to provide a microporous filter for intravenous fluid that is easy to assemble with little waste and at low cost.

These and other objects are set forth in the following detailed description of the preferred embodiment of the present invention as shown in the attached drawings, of which:

Figure 1:
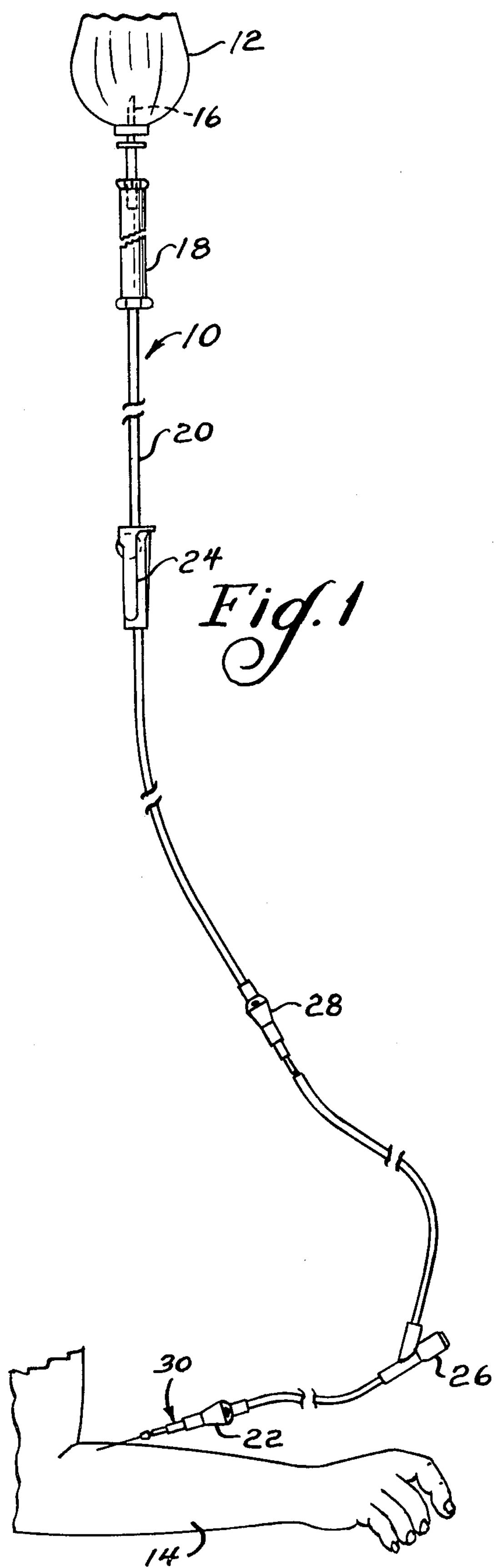
FIG. 1 is an elevational view of an intravenous fluid administration set employing a filter in accordance with the present invention.

The present invention is generally embodied in an intravenous fluid administration set 10 as an in-line filter for removing any microscopic particulate from the fluid stream as it is administered to the patient. However, the present filter may also be used in other than fluid administration sets. For example, it may be employed as a syringe filter for direct attachment to the end of a syringe. In the illustrated embodiment, the filter is employed in an otherwise typical fluid administration set for conveying parenteral fluids or the like from an elevated fluid reservoir 12 to a patient 14 by gravity flow. The upper end of the administration set 10 terminates in a puncturing spike 16 for entry through a permeable membrane in the fluid reservoir 12. Fluid from the reservoir is conveyed, by gravity, downwardly through a drip chamber 18, a length of plastic tubing 20 and terminating in a combination blood flashback indicator and injection site 22, sold under the trademark FLASHBALL by Travenol Laboratories, Inc. of Deerfield, Illinois. The flow of liquid through the tubing is typically controlled by a roller clamp 24 which compresses the tubing to control the size of the lumen. Additional injection sites 26 or combination blood flashback indicators and injection sites 28 may also be provided along the length of plastic tubing to permit the addition of medication or the connection of other administration sets.

In accordance with the present invention a unique and remarkably easy-to-assemble filter, generally at 30, is provided in the fluid administration set to remove any microscopic particulate or the like from the fluid as it is administered to a patient. This filter employs a normally, hydrophobic or liquid-repellent sintered plastic depth-filtering element 32 to filter the liquid and remove any particulate from the fluid stream. Because the material is hydrophobic, it would not be ordinarily considered for filtering aqueous solutions. However, as set forth in more detail hereinafter, it has been found that with a unique pore size and volume of pores, also called void volume, within the filter element, satisfactory gravitationally-induced liquid flow rates may be provided to the patient despite the hydrophobic nature of the material, while the tortuous passageways in the filter remove microscopic particulate. Because of the relatively large pore sizes used (20 microns or greater), in combination with the normally hydrophobic material, any gas is able to pass through the filter element, which therefore does not "air-block".

Figure 2:
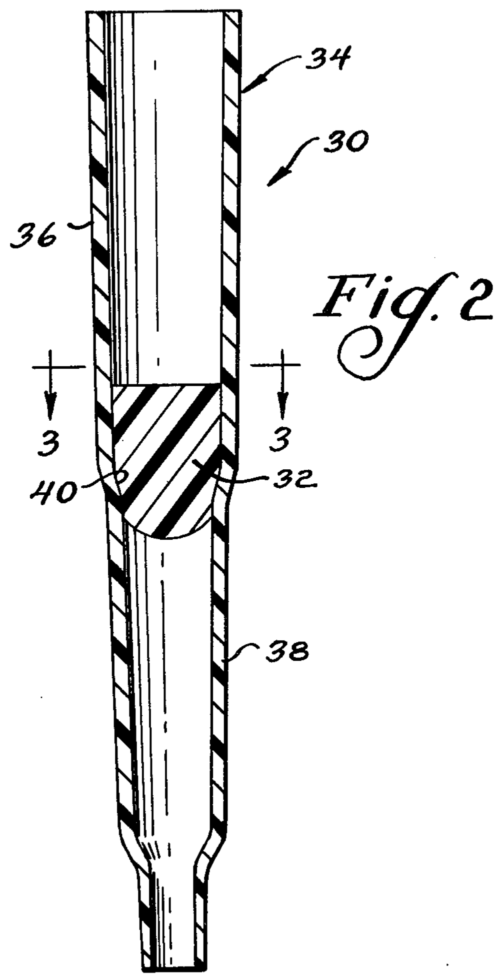
FIG. 2 is a vertical cross-sectional view of the filter embodying the present invention.
Figure 3:
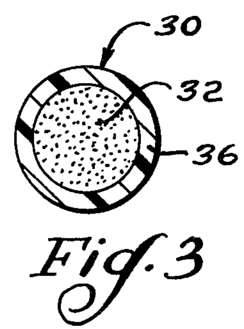
FIG. 3 is a cross-sectional view of the filter in FIG. 2, taken along line 3—3.

Turning now to a more detailed description of the preferred embodiment of the present invention, FIG. 2 is a cross-sectional view of the filter embodying the present invention. The filter device 30 generally has a clear, rigid plastic housing 34 constructed of polycarbonate or other medically approved materials such as polyethylene, polypropylene or the like. The housing is generally tubular shaped with a larger diameter portion 36 merging into a smaller diameter portion 38 to define an angled shoulder 40 therebetween. The smaller diameter portion terminates in a further size reduction for attachment, as by solvent sealing, to the plastic tubing 20 of the administration set. The large end of the tubular housing is secured by simple friction or solvent bonding to the end of the elastomeric blood flashback indicator 22. The tubular housing could also be attached directly to the plastic tubing if the set does not include a flashback indicator.

The filter element 32 is frictionally mounted within the bore of the tubular plastic housing 34, preferably in compressive engagement with the internal shoulder 40 to provide a tight seal between the housing and filter element. The filter element itself is a unitary, bullet-shaped plug of sintered hydrophobic plastic material suitable for medical applications and having an average pore size sufficiently small to filter out microscopic particulate but a volume of pores sufficiently large to provide adequate flow rates in a gravitationally-induced flow system. This type of filter is to be contrasted with a membrane filter which has very small pores spread over a large surface area. In a depth-type filter of the type shown by element 32, the pore size may be substantially larger than for a membrane filter but the tortuous passageways encountered in passing through the filter plug removes any microscopic particulate from the liquid being filtered.

Preferably, the filter element 32 in the present invention is a high density sintered polyethylene which is medically benign. One such material which has been found to be particularly effective as a fluid filter is available under the trademark "POREX" from Glasrock Products, Inc. of Fairburn, Georgia. Such material is normally hydrophobic or liquid repellent which makes it additionally novel for use as an intravenous fluid filter in a gravity flow administration set. It is also slightly compressible to form a tight fit within the tubular housing 34. The nature of this material, and its use as a filter for liquid reagents, is set forth in U.S. Pat. No. 3,744,640. Additionally, sintered polyethylene purchased from Glasrock has been used as a gas-permeable sterile barrier, set forth in U.S. patent application Ser. No. 953,576, filed Oct. 23, 1978; as a bubble generator in a medical humidifier, i.e., air is forced through a submerged sintered polyethylene element, which disperses the air and allows it to bubble upwardly through the liquid for humidification; and the material has further been used to vent air from a blood flashback chamber in a catheter, for example, U.S. patent application Ser. No. 813,890, filed July 8, 1977. An extremely large pore size sintered polyethlene filter plug has also been used as a serum blood filter.

As noted earlier, with the sintered hydrophobic plastic filter member, selection of pore size and pore volume is important to obtaining proper filtration and yet sufficient liquid flow rate through an otherwise liquid-repellent member. Although other measures of filtration have been suggested, one definition of microporous filtration which has been used with the present invention is 90% filtration efficiency of 5 micron particles. In determining flow rates using this measure of filtration efficiency it should be noted that the height of the fluid reservoir 12 above a patient in a typical administration set of the type shown in FIG. 1 is about thirty (30) inches, although it may be varied somewhat depending on the circumstances and the desired flow rate. Typical patient injection flow rates may be from about 100 to about 300 c.c./hr., with some critical patients requiring up to 500 c.c./hr. Of course, these flow rates may vary, depending on conditions such as patient vascular pressure, needle size and solution viscosity. But generally, a filter should provide microporous filtration while allowing flow rates of at least 100 to 300 c.c./hr., and preferably up to 500 c.c./hr., under about 30 inches of head pressure. As indicated above, the liquid column height could be raised somewhat to assist in achieving the higher flow rates.

In the present invention, the selection of the pore size and the relative volume of pores to obtain appropriate flow rates and filtration may vary, depending on the size and shape of the element. For example, if the filter element has a large surface area perpendicular to the flow stream, a smaller void volume may be used without restricting the flow rate too much. If the filter element is relatively long in the same direction as liquid flow, with a longer tortuous path through which the liquid must pass, a larger pore size may be selected without impairing the microporous filtration. More specifically, for a sintered hydrophobic plastic filter element in accordance with the present invention which has a filtration surface area of from about 0.04 to 0.2 square inches and a length of from $\frac{1}{8}$ to $\frac{3}{4}$ inches, the presently preferred range of mean pore sizes is from about 20 to 40 microns, with a relative void volume of about 40% to 65% to obtain microporous filtration while maintaining sufficient flow rates. Although a variety of filter configurations may be selected from these ranges, the relative relationship is that the smaller pore size is used with the shorter length filter and the smaller void volume is used with the larger surface area or larger mean pore size.

At least two combinations of filter area, length, pore size and pore volume within the ranges described above have been particularly satisfactory. Employing POREX sintered polyethylene filter elements, it has been found that with a cylindrical, bullet-shaped filter plug of the shape shown in the drawings, having a diameter of about 0.25 inches and a total length of about 0.34 inches, adequate flow rates and microporous filtration were obtained in one filter plug having a mean pore size of 20 microns and a void volume of 63% and in another having a mean pore size of 35 microns and a void volume of 45%. In addition, these filters evidenced very high retention capacity for the particulates while maintaining a satisfactory flow rate.

In summary, it may be seen that the present invention provides a uniquely easy-to-assemble but effective in-line filter for intravenous fluid. The sintered plastic filter element is a normally hydrophobic material, not ordinarily considered for filtering liquids, but with a selected pore size and void volume which provides microporous filtration without reducing flow rates and which, aided by the hydrophobic property, does not "air-block".

The present invention has been described in terms of the preferred embodiment for the purpose of illustration and not limitation, and as set forth in the following claims, it is intended to include those equivalent structures, some of which may be apparent upon reading this description, and others that may be obvious only after some study.

What is claimed is:

1. In a parenteral fluid administration set comprising fluid conduit means including housing means defining a flow path for conveying liquid between a parenteral fluid reservoir and a patent, the improvement comprising a unitary hydrophobic plastic depth filter element carried within said flow path in said housing means to filter liquid passing therethrough, said depth filter having a mean pore size between about 20 and 40 microns, inclusive, and a void volume between about 40% and 65%, inclusive, so as to permit a fluid flow rate of at least 100 c.c./hr. with about 30 inches of fluid head pressure.

2. A parenteral fluid administration set in accordance with claim 1 wherein said depth filter element is made of polyethylene material.

3. A parenteral fluid administration set in accordance with claim 1 wherein said depth filter element is made of sintered plastic material.

4. A parenteral fluid administration set in accordance with claim 1 wherein said depth filter element is made of high density polyethylene material.

5. A parenteral fluid administration set in accordance with claim 1 wherein said depth filter element has a void volume of about 63% and a mean pore size of about 20 microns.

6. A parenteral fluid administration set in accordance with claim 1 wherein said depth filter element has a void volume of about 45% and a mean pore size of about 35 microns.

7. A parenteral fluid administration set in accordance with claim 1 wherein said depth filter element is carried in a relatively rigid housing having an inlet, an outlet, and a passageway defined therebetween, said filter element being slightly larger than said passageway and compressible for frictional retention therewithin.

8. A parenteral fluid administration set in accordance with claim 1 wherein said depth filter element has a filtration surface area of between about 0.04 and about 0.2 square inches, inclusive, and a length of between about 0.125 to about 0.75 inches, inclusive.

9. A filter device for filtering medical fluids comprising housing means defining an inlet, an outlet and a flow path therebetween, a unitary hydrophobic plastic depth filter element carried in said flow path to filter fluid passing therealong, said depth filter element having a mean pore size between about 20 and 40 microns, inclusive, and a void volume of between about 40% and 65%, inclusive, so as to permit a fluid flow rate of at least 100 c.c./hr. with about 30 inches of fluid head pressure.

10. A filter device in accordance with claim 9 wherein said depth filter element is made of polyethylene.

11. A filter device in accordance with claim 9 wherein said depth filter element is made of high density polyethylene.

12. A filter device in accordance with claim 9 wherein said depth filter element is made of sintered plastic material.

13. A filter device in accordance with claim 9 wherein said depth filter element has a void volume of about 63% and a mean pore size of about 20 microns.

14. A filter device in accordance with claim 9 wherein said depth filter element has a void volume of about 45% and a mean pore size of about 35 microns.

15. A filter device in accordance with claim 9 wherein said housing means is relatively rigid, and said filter element is larger than said flow path and slightly compressible for frictional retention within said flow path.

16. A filter device in accordance with claim 9 wherein said filter element has a filtration surface area between about 0.04 and 0.2 square inches, inclusive, and a length of from about 0.125 to 0.75 inches, inclusive.

17. In a medical fluid administration set comprising fluid conduit means including housing means defining a flow path for conveying liquid between a medical fluid reservoir and a patient, the improvement comprising a unitary polyethylene depth filter element carried within said flow path in said housing means to filter liquid passing therealong, said depth filter element having a filtration surface area between about 0.04 and 0.2 square inches, inclusive, a length from about 0.125 to 0.75 inches, inclusive, a mean pore size between about 20 and 40 microns, inclusive, and a void volume between about 40% and 65%, inclusive, so as to permit a fluid flow rate of at least 100 c.c./hr. with about 30 inches of fluid head pressure.

18. A medical fluid administration set in accordance with claim 17 wherein said depth filter element has a void volume of about 63% and a mean pore size of about 20 microns.

19. A medical fluid administration set in accordance with claim 17 wherein said depth filter has a void volume of about 45% and a mean pore size of about 35 microns.

20. A medical fluid administration set in accordance with claim 17 wherein said depth filter element is carried in a relatively rigid housing having an inlet, an outlet and a flow path therebetween, said filter element being slightly larger than said flow path and compressible for frictional retention therewithin.

21. A filter device for filtering medical fluids comprising housing means defining an inlet, an outlet and a fluid flow path therebetween, a unitary polyethylene depth filter element carried in said flow path to filter fluid passing therealong, said filter element having a filtration surface area between about 0.04 and 0.2 square inches, inclusive, a length from about 0.125 to 0.75 inches, inclusive, a mean pore size between about 20 and 40 microns, inclusive, and a void volume between about 40% and 65%, inclusive, so as to permit a fluid flow rate of at least 100 c.c./hr. with about 30 inches of fluid head pressure.

22. A filter device in accordance with claim 21 wherein said depth filter has a void volume of about 63% and a mean pore size of about 20 microns.

23. A filter device in accordance with claim 21 wherein said depth filter element has a void volume of about 45% and a mean pore size of about 35 microns.

24. A filter device in accordance with claim 21 wherein said housing means is relatively rigid and said filter element is slightly larger than said flow path and compressible for frictional retention therewithin.

* * * * *